United States Patent

[11] 4,320,128
[45] Mar. 16, 1982

Fake

[54] CHROMANONE DERIVATIVES AND COMPOSITIONS CONTAINING THEM

[75] Inventor: Charles S. Fake, Harlow, England
[73] Assignee: Beecham Group Limited, England
[21] Appl. No.: 131,236
[22] Filed: Mar. 17, 1980

[30] Foreign Application Priority Data

Mar. 24, 1979 [GB] United Kingdom ............... 10405/79
Feb. 9, 1980 [GB] United Kingdom ............... 04407/80

[51] Int. Cl.³ .................... A61K 31/44; C07D 405/12; C07D 405/14
[52] U.S. Cl. .................................. 424/250; 544/360; 544/376
[58] Field of Search ................. 544/376, 360; 424/250

[56] References Cited

U.S. PATENT DOCUMENTS

| | | | |
|---|---|---|---|
| 3,637,759 | 1/1972 | Weichet et al. | 544/376 |
| 4,092,416 | 5/1978 | Winter et al. | 544/376 |
| 4,092,631 | 6/1978 | Gardner | 544/376 |

FOREIGN PATENT DOCUMENTS

| | | | |
|---|---|---|---|
| 2123923 | 11/1972 | Fed. Rep. of Germany | 544/376 |
| 2123924 | 11/1972 | Fed. Rep. of Germany | 544/376 |
| 2555290 | 6/1977 | Fed. Rep. of Germany | 544/376 |
| 1184762 | 3/1970 | United Kingdom | 544/376 |

*Primary Examiner*—Donald G. Daus
*Assistant Examiner*—James H. Turnipseed
*Attorney, Agent, or Firm*—Jacobs & Jacobs

[57] ABSTRACT

Compounds of the formula (II):

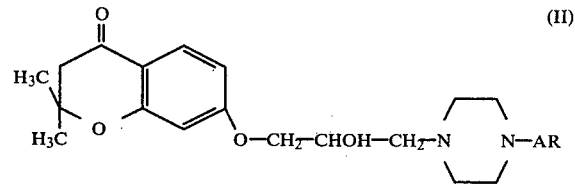

and pharmaceutically acceptable acid-addition salts thereof wherein Ar is a pyridyl or optionally substituted phenyl group of the sub-formula $-C_6H_3R_1R_2$ wherein $R_1$ is a hydrogen, fluorine, chlorine or bromine atom or a lower alkyl, lower alkoxyl, lower acyl, lower acyloxyl or lower alkoxycarbonyl group; and $R_2$ is a hydrogen, fluorine or chlorine atom or a lower alkyl or lower alkoxy group having useful anti-hypertension activity, their preparation, and pharmaceutical compositions containing them.

6 Claims, No Drawings

CHROMANONE DERIVATIVES AND COMPOSITIONS CONTAINING THEM

This invention relates to chromanone derivatives, a process for the preparation, compositions containing them.

U.K. Pat. No. 1,357,633 discloses that compounds such as those of the formula (I):

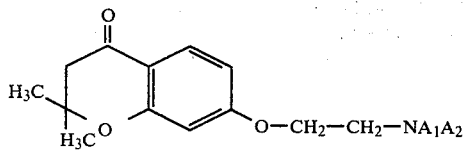

wherein $A_1$ and $A_2$ are lower alkyl groups which may be linked possess mood modifying activity. It has now been found that if the $CH_2CH_2NA_1A_2$ moiety is replaced by a hydroxypropyl-substituted piperazine moiety then the resulting compounds possess a completely different type of activity, namely antihypertensive activity.

Accordingly, the present invention provides compounds of the formula (II):

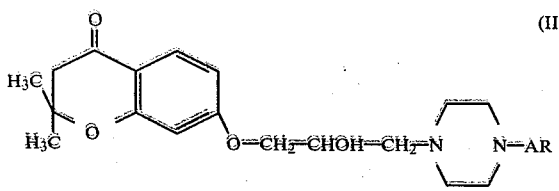

and pharmaceutically acceptable acid-addition salts thereof wherein Ar is a pyridyl or optionally substituted phenyl group of the sub-formula $=C_6H_3R_1R_2$ wherein $R_1$ is a hydrogen, fluorine, chlorine or bromine atom or a lower alkyl, lower alkoxyl, lower acyl, lower acyloxyl or lower alkoxycarbonyl group; and $R_2$ is a hydrogen, fluorine or chlorine atom or a lower alkyl or lower alkoxyl group.

When used herein the term "lower" means that the group contains not more than 3 carbon atoms. When used herein the term "acyl" means unsubstituted carboxylic acyl.

Suitably Ar is a pyridyl group such as the 2-pyridyl group.

Aptly Ar is an optionally substituted phenyl group.

Often when Ar is $=C_6H_3R_1R_2$ the group $R_1$ will be hydrogen. Suitably in such cases $R_2$ is ortho to the point of attachment of the phenyl ring to the piperazine.

A particularly suitable value for $R_1$ and $R_2$ is hydrogen and alkoxy respectively. In such cases $R_2$ is preferably methoxy, most preferably ortho-methoxy.

From the aforesaid it will be appreciated that one sub-group of compounds of interest within formula (II) is of formula (III):

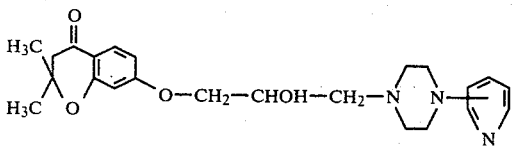

and pharmaceutically acceptable salts thereof.

In formula (III) the pyridyl group is preferably 2-pyridyl.

A second sub-group of interest is of formula (IV):

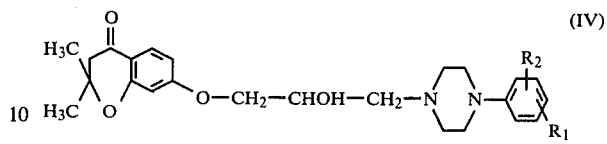

wherein $R_1$ and $R_2$ are as defined, and pharmaceutically acceptable salts thereof.

Aptly in formula (IV) $R_1$ is hydrogen.

Suitable and preferred examples of $R_2$ in formula (IV) are as hereinbefore described in relation to formula (II).

One group of compounds within formula (IV) is of formula (V):

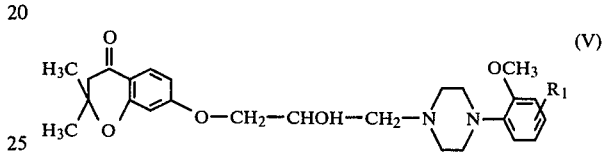

and the pharmaceutically acceptable salts thereof wherein $R_1$ is as defined in relation to formula (II).

A particularly suitable value for $R_1$ in relation to formula (V) is the hydrogen atom.

The compounds of the invention are most suitably provided in the form of an acid addition salt with a pharmaceutically acceptable acid. Such salts may be mono-acid addition salts or more conveniently di-acid addition salts. Suitable pharmaceutically acceptable acids include inorganic and organic acids such as hydrochloric, phosphoric, sulphuric, methane sulphonic acetic, propionic, citric, lactic, succinic, glyconic and the like. Favoured salts include the hydrochloride salts such as the di-hydrochloride salt.

Salts of the compounds of the formula (II) are generally more suitable than the correponding free base on account of their crystalline nature which renders them of improved stability.

The compounds of this invention may be provided in the form of solvates such as hydrates.

The compounds of this invention may be made and used as a single optical isomer or as a mixture of optical isomers such as a racemic mixture.

The present invention also provides a pharmaceutical composition which comprises a compound of this invention as hereinbefore described together with a pharmaceutically acceptable carrier.

The compositions of this invention may be adapted for administration by injection if required but it is normally preferred that they are in a form suitable for oral adminstration. Oral dosage forms may contain such conventional excipients such as fillers, lubricants, disintegrants, binders, preservatives. colourants and so on. Suitable fillers include lactose, microcrystalline cellulose, calcium phosphate, manitol and the like. Suitable lubricants include magnesium stearate and stearic acid. Suitable disintegrants include polyvinylpolypyrrolidone and sodium starch glycollate.

The oral dosage forms are normally provided as discrete forms such as tablets and capsules. In general such unit doage forms will contain from 5 to 500 mg and more usually from 25 to 300 mg. These unit dosage forms may be administered from 1 to 6 times daily in such a way that the daily dose for a 70 kg adult will normally be between 30 to 1,500 mg and more usually from 100 to 1,000 mg for example from 200 to 800 mg.

In another aspect this invention provides a process for the preparation of a compound of this invention which process comprises the reaction of 1,2-epoxy-3-(2,2-dimethylchroman-4-on-7-yl)oxypropane with a compound of the formula (VI):

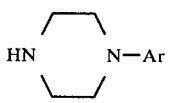
(VI)

wherein Ar is as defined in relation to formula (II) and thereafter reacting with an acid if an acid addition salt is required.

The condensation reaction is normally carried out in a lower alkanol such as ethanol at an elevated temperature, for example under reflux. The crude compound of the formula (II) may be obtained by evaporation of the solvent. If desired this initial product may be purified by chromatography or other conventional methods but in general it is more convenient to convert the free base into a salt which may then be purified by crystallization and recrystallization. In general a di-salt is preferred since it is more easily prepared by using a slight excess of the acid.

Compounds prepared by this process are normally racemic. The racemic mixture may be resolved using an optically active acid in conventional manner, for example as in L. F. Fieser and M. Fieser, "Organic Chemistry", 3rd Ed., 1956, Reinhold; S. H. Wilen "Tables of Resolving Agents and Optical Resolutions", University of Notre Dame Press, 1972, or S. H. Wilen, "Topics in Stereochemistry", 1971, Vol 6, John Wiley, N.Y.

The useful intermediate 1,2-epoxy-3-(2,2-dimethylchroman-4-on-7-yl)oxypropane forms part of this invention. The compound may be prepared as described in Example 1.

The following Examples illustrate the invention.

EXAMPLE 1

Preparation of Intermediate
1,2-Epoxy-3-(2,2-dimethylchroman-4-on-7-yl)oxypropane 2,2-Dimethyl-7-hydroxychroman-4-one (31.5 g), epichlorohydrin (130 ml), potassium carbonate (45.35 g) and dry acetone (130 ml) were stirred and refluxed for 16 hours. The mixture was filtered hot and the filtrate evaporated to dryness under reduced pressure to give the epoxide (40.53 g) as a white solid of m.p. 62°–65° C.

N.M.R. (CDCl$_3$/TMS): $\delta = 1.43$ (s, 6H; 2.60 (s, 2H) overlapped with 2.60–4.50 (m, 5H); 6.34 (d, J=2 Hz, 1H) overlapped with 6.51 (q, J=8, 2 Hz, 1H); 7.73 (d, J=8 Hz, 1H).

I.R. (Nujol Mull): 1670 cm$^{-1}$ (C=O).

In the following Examples the compounds prepared have the general formula:

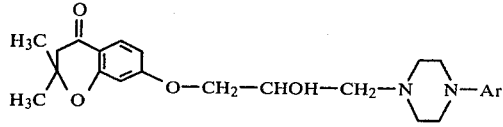

EXAMPLE 2

1-(4-(o-Methoxyphenyl)-piperazino)-3-(2,2-dimethylchroman-4-on-7-yl)oxypropan-2-ol and its Dihydrochloride

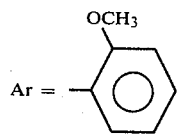

1,2-Epoxy-3-(2,2-dimethylchroman-4-on-7-yl)oxypropane (10.00 g) and N-(o-methoxyphenyl)-piperazine (7.07 ml) were refluxed in ethanol (250 ml) for 3 hours. The solution was evaporated to dryness in vacuo to give the aminoalcohol (17.31 g), as a light brown gum.

N.M.R. (CDCl$_3$/TMS): $\delta=1.41$ (s,6H); 2.63 (s, 2H) overlapped with 2.30–4.40 (m, 16H) overlapped with 3.86 (s, 3H); 6.43 (d, J=2 Hz, 1H) overlapped with 6.58 (q, J=8, 2Hz, 1H); 6.91 (s, 4H); 7.79 (d, J=8 Hz, 1H).

The free base was dissolved in ethanol and addition of excess ethereal-HCl precipitated the crude salt. One recrystallization from ethanol gave the dihydrochloride as a white crystalline hemihydrate (7.43 g). m.p. 197°–199° C.

$C_{25}H_{32}N_2O_5 \cdot 2HCl \cdot \frac{1}{2}H_2O$ requires: C, 57.47; H, 6.75; N, 5.36; Cl, 13.57, Found: C, 57.35; H, 6.61; N, 5.41; Cl, 13.66%.

EXAMPLE 3

1-(4-(o-Ethoxyphenyl)-piperazino)-3-(2,2-dimethylchroman-4-on-7-yl)oxypropan-2-ol hydrochloride

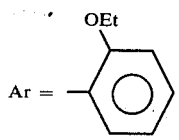

1,2-Epoxy-3-(2,2-dimethylchroman-4-on-7-yl)-oxypropane (3.0 g) and N-(o-ethoxyphenyl)-piperazine (2.17 g) were heated under reflux in isopropanol (20 ml) for 3 hours. The solution was evaporated to dryness in vacuo and treated with an excess of ethanolic hydrogenchloride and evaporated to dryness in vacuo. The residue was recrystallized from isopropanol-ether to give 1-(4-(o-ethoxyphenyl)-piperazino)-3-(2,2-dimethylchroman-4-on-7-yl)oxypropan-2-ol 1.66 hydrochloride (2.8 g), m.p. 193°–5° C.

Anal. $C_{26}H_{24}N_2O_5$ 1.66 HCl required: C, 60.65; H, 7.0; N, 5.45; Cl, 11.4%. Found: C, 60.35; H, 7.05; N, 5.45: Cl, 11.4%.

N.M.R. (d$_6$DMSO+CDCl$_3$): $\delta$ 1.43 (s) and 1.45 (t, J=6 Hz) total 9H; 2.65 (2H, s); 3.2–4.2 (m) and 4.15 (q, J=6 Hz) total 14H; 4.6 (1H, m); 6.4–7.4 (6H, m); and 7.7 (1H, d, J=8 Hz).

EXAMPLE 4

1-(4-(Chlorophenyl)-piperazino-3-(2,2-dimethylchroman-4-on-7-yl)oxypropan-2-ol hydrochloride

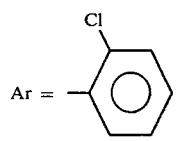

1,2-Epoxy-3-(2,2-dimethylchroman-4-on-7-yl)oxypropane (7.6 g) and N-(o-chlorophenyl)-piperazine (6.04 g) were heated under reflux in ethanol (150 ml) for 3 hours. The solution was evaporated to dryness in vacuo and treated with an excess of ethanolic hydrogen chloride and evaporated to dryness in vacuo. The residue was crystallised from ethanol/ether to give 1-(4-(o-chlorophenyl)-piperazino)-3-(2,2-dimethylchroman-4-on-7-yl)oxypropan-2-ol hydrochloride (11.07 g), m.p. 169°–173° C.

Anal. $C_{24}H_{29}N_2O_4Cl\cdot HCl$ required: C, 59.85; H, 6.30; N, 5.8; Cl, 14.75%. Found: C, 59.7; H, 6.05; N, 5.7; Cl, 14.6%.

N.M.R. ($CDCl_3$): δ 1.43 (6H, s); 2.65 (2H, s); 3.1–4.4 (12H, m); 4.7 (1H, m); 6.3–7.5 (6H, m) and 7.7 (1H, d, J=8 Hz).

EXAMPLE 5

1-(4-(2'-Pyridyl)-piperazino)-3-(2,2-dimethylchroman-4-on-7-yl)-oxypropan-2-ol-dihydrochloride ethanol (1:1)

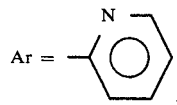

1,2-Epoxy-3-(2,2-dimethylchroman-4-on-7-yl)oxypropane (3.0 g) and N-(2'-pyridyl)-piperazine(1.97 g) were stirred at room temperature in ethanol (100 ml) for 24 hours). The solution was evaporated to dryness in vacuo and treated with an excess of ethanolic hydrogen chloride and evaporated to dryness in vacuo. The residue was crystallised from ethanol/ether to give 1-(4-(2'-pyridyl)-piperazino)-3-(2,2-dimethylchroman-4-on-7-yl)-oxypropan-2-ol dihydrochloride ethanol (1:1) (5.3 g), m.p. 148°–150° C.

Anal. $C_{23}H_{29}N_3O_4\cdot 2HCl\cdot C_2H_5OH$ required: C, 56.6; H, 7.05; N, 7.9; Cl, 13.4%. Found: C, 56.05; H, 7.1; N, 7.95; Cl, 13.45%.

N.M.R. ($D_2O$): δ 1.1 (3H, t, J=7 Hz); 1.4 (6H, s); 2.6 (2H, s); 3.6 (q, J=7 Hz) and 3.5–4.6 (m) total 15H; 6.3–8.2 (7H, m).

BIOLECT ACTIVITY

The biological activity of the compounds of this invention is illustrated by the following test:

Systolic blood pressures were recorded by a modification of the tail cuff method described by I. M. Claxton, M. G. Palfreyman, R. H. Poyser and R. L. Whiting, European Journal of Pharmacology, 37, 179 (1976). An oscilloscope or W+W BP recorder, model 8002, was used to display pulses. Prior to all measurements rats were placed in a heated environment (33.5±0.5° C.) before transfer to a restraining cage. Each determination of blood pressure was the mean of at least 6 readings. Groups of six spontaneously hypertensive rats (aged 12–18 weeks) with systolic blood pressures >170 mmHg were used.

The following results were obtained:

| Compound of Example No. | Time Post Dose (hrs) | % Change in Systolic Blood Pressure | % Change in Heart Rate |
|---|---|---|---|
|  | Initial Values | 207 ± 2 mmHg | 450 ± 11 beats/min |
| 2 (DiHCl) at 100 mg/kg p.o. | 1 | −28 ± 3 | −3 ± 6 |
|  | 2 | −38 ± 3 | −5 ± 5 |
|  | 4 | −44 ± 3 | −2 ± 3 |
|  | 6 | −36 ± 2 | −1 ± 2 |
|  | 24 | −4 ± 2 | −1 ± 2 |
|  | Initial Values | 213 ± 5 | 485 ± 9 beats/min |
| 3 at 100 mg/kg p.o. | 1 | −15 ± 4 | 0 ± 7 |
|  | 2 | −19 ± 6 | 3 ± 5 |
|  | 4 | −25 ± 5 | −2 ± 6 |
|  | 6 | −≅± 5 | −1 ± 4 |
|  | 24 | −4 ± 3 | −3 ± 4 |
|  | Intial Values | 216 ± 2 | 470 ± 22 |
| 4 at 100 mg/kg p.o. | 1 | −29 ± 2 | −16 ± 3 |
|  | 2 | −34 ± 3 | −5 ± 6 |
|  | 4 | −21 ± 1 | 11 ± 6 |
|  | 6 | −11 ± 4 | 9 ± 7 |
|  | 24 | 0 ± 1 | 2 ± 3 |
|  | Initial Values | 231 ± 5 | 456 ± 13 |
| 5 at 10 mg/kg p.o. | 1 | −21 ± 3 | 5 ± 1 |
|  | 2 | −18 ± 4 | 1 ± 3 |
|  | 4 | −18 ± 3 | 3 ± 2 |
|  | 6 | −19 ± 3 | 2 ± 4 |
|  | 24 | −4 ± 2 | −4 ± 3 |

The above data shows that the test compounds were able to effect good fall in blood pressure without significant effects on heart rate. This may reflect the α blocking effects of the test compounds.

TOXICITY

No toxic effects were observed in these tests.

I claim:

1. A compound of formula (II):

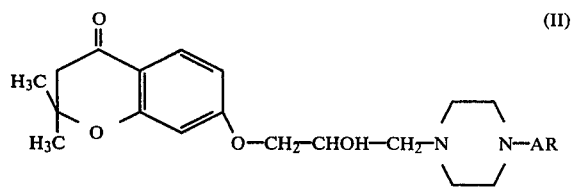

or a pharmaceutically acceptable acid-addition salt thereof wherein Ar is pyridyl or $-C_6H_3R_1R_2$ wherein $R_1$ is hydrogen, fluorine, chlorine, bromine, lower alkyl, lower alkoxyl, lower carboxylic acyl, lower carboxylic acyloxyl or lower alkoxycarbonyl; and $R_2$ is hydrogen, fluorine, chlorine, lower alkyl or lower alkoxyl.

2. A compound according to claim 1, wherein Ar is 2-pyridyl.

3. A compound according to claim 1, wherein Ar is $-C_6H_3R_1R_2$ wherein $R_1$ is hydrogen and $R_2$ is ortho.

4. 1-(4-(o-Methoxyphenyl)-piperazino)-3-(2,2-dimethylchroman-4-on-7-yl)oxypropan-2-ol, and pharmaceutically acceptable salts thereof.

5. A pharmaceutical composition for the treatment of hypertension, comprising an effective amount of a compound according to claim 1, together with a pharmaceutically acceptable carrier.

6. A method of treatment of hypertension, which method comprises administering to the sufferer an effective amount of a compound according to claim 1.

* * * * *